United States Patent [19]
Yoshida et al.

[11] Patent Number: 5,234,681
[45] Date of Patent: Aug. 10, 1993

[54] ULTRAVIOLET RAY-ABSORBING COSMETIC COMPOSITION

[75] Inventors: Norio Yoshida, Ibaraki; Masato Sugiura; Fumitoshi Sugiura, both of Gamagori, all of Japan

[73] Assignees: Teijin Limited, Osaka; Takemoto Oil & Fat Co., Ltd., Aichi, both of Japan

[21] Appl. No.: 854,577

[22] Filed: Mar. 20, 1992

Related U.S. Application Data

[63] Continuation-in-part of Ser. No. 474,100, Apr. 17, 1990, abandoned.

[30] Foreign Application Priority Data

Aug. 19, 1988 [JP] Japan ................ 63-204596

[51] Int. Cl.$^5$ .................. A61K 7/42; A61K 7/48; A61K 9/10; A61K 9/14
[52] U.S. Cl. ................ 424/59; 424/DIG. 5; 424/63; 424/69; 514/828; 514/847; 514/873; 514/937; 514/938
[58] Field of Search ................. 424/59, 60

[56] References Cited

U.S. PATENT DOCUMENTS 4,061,730 12/1977 Kalopissis et al. ................ 424/59
4,446,262 5/1984 Okumura et al. ................ 524/89
4,489,057 12/1984 Welters et al. ................ 424/47

FOREIGN PATENT DOCUMENTS 2301524 9/1976 France ................ 514/256

OTHER PUBLICATIONS

Chem. Abs., 1983, vol. 98 144526x, Okumura et al. corresponds to U.S. Pat. No. 4,446,262, cited by applicant.
Chem. Abs., 1970, vol. 72, 13378r, Yoda et al.
Patent Abstracts of Japan, vol. 11, No. 163 (C-424) [2610], May 26, 1987.

Primary Examiner—Dale R. Ore
Attorney, Agent, or Firm—Wenderoth, Lind & Ponack

[57] ABSTRACT

The cosmetic composition of this is an ultraviolet ray-absorbing cosmetic composition containing particles of cyclic imino ester which is excellent in ultraviolet ray absorbability, stable against water, sparingly soluble in organic solvents, fats and oils, sebum, etc., and further has only a low skin-irritating property. When this cosmetic composition is applied onto the skin, erythema is not formed on/in the skin even if it is exposed to sunlight for a long period, and further aging of the skin can be prevented.

4 Claims, 1 Drawing Sheet

ULTRAVIOLET RAY-ABSORBING COSMETIC COMPOSITION

CROSS-REFERENCE TO RELATED APPLICATION

This application is a continuation-in-part of copending application U.S. Ser. No. 07/474,100 filed on Apr. 17, 1990, now abandoned, which is a national phase application phase application based on International Application No. PCT/JP89/00842 filed on Aug. 18, 1989.

TECHNICAL FIELD

This invention relates to an ultraviolet ray-absorbing cosmetic composition. More specifically, this invention relates to an ultraviolet ray-absorbing cosmetic composition for application to skin containing a certain kind of cyclic imino ester as an ultraviolet absorber.

TECHNICAL BACKGROUND

Although sunbathing is frequently performed for improvement of health, it is known that erythema is formed by excessively exposing the skin to sunlight and that this phenomenon is caused mainly by light beam of a wavelength of 280 to 320 nm, so-called UV-B. For the purpose of prevention of occurrence of such a burn symptom, it is proposed to compound ultraviolet absorber having absorption in the region of UV-B (Please refer to the gazette of Japanese Patent Publication No. 39404/1984 and the specification of the corresponding U.S. Pat. No. 4,061,730).

On the other hand, it has been thought that light beam having a wavelength of 320 to 400 nm (UV-A), which makes the skin brown without causing erythema, is a desirable light. However, it has been revealed that while UV-B reaches only up to the epithelial layer, UV-A reaches up to the dermal layer, a deeper layer, and therefore, aging of skin is accelerated by long-term exposure to UV-A.

Therefore, cosmetics wherein a compound having an absorption band in the region of UV-A is compounded have come to be eagerly sought, and substituted dibenzoylmethanes have been proposed as compounds having such effects (Please refer to the gazette of Japanese Patent Publication No. 4813/1986 and the specification of U.S. Pat. No. 4,489,057). However, the substituted dibenzoylmethanes cannot exhibit sufficient effect since their absorption ability rapidly decreases at 350 nm or more. Further, their water resisting stability is not sufficient and improvement in sustainability of effect has been desired.

Further, the specification of U.S. Pat. No. 4,446,262 discloses a light-stabilized polymer composition containing an ultraviolet absorber compound represented by the following formula (I)

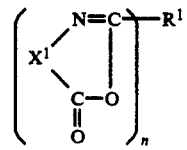

wherein $X^1$ is 1,2-phenylene, 1,2-naphthylene, 2,3-naphthylene, a group represented by the following formula (a)

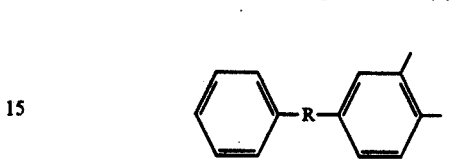

(wherein, R is —O—, —CO—, —S—, —SO$_2$—, —CH$_2$— or —(CH$_2$)$_2$— or —C(CH$_3$)$_2$—) or a group represented by the following formula (b)

(wherein, R is as defined above);
n is 1, 2 or 3; and $R^1$ is a n-valent hydrocarbon. This composition aims at using the above compound as protection against deterioration, due to exposure to ultraviolet ray, of the polymer base material itself, for example, thermoplastic resin such as polyester, polyamide, polycarbonate, polyolefin, polyether or polysulfone, or thermosetting resin such as phenolformaldehyde resin, melamine resin, polyurethane resin, epoxy resin or unsaturated polyester resin. This U.S. Patent specification has no disclosure about a cosmetic composition directed to a protective object utterly different from protection of polymer base material itself.

An object of this invention is to provide an ultraviolet ray-absorbing cosmetic composition for application to skin.

Another object of the invention is to provide an ultraviolet ray-absorbing cosmetic composition containing a cyclic imino ester compound which is not only sufficiently safe when it is directly applied onto the skin of human beings, but also colorless, odorless and non-irritating.

Still another object of the invention is to provide an ultraviolet ray-absorbing cosmetic composition which is non-volatile, has a chemically stable property not to decompose by sweating or washing, and moreover is stable against sunlight and sustains its ultraviolet ray-absorbing ability over a long time.

Still another object of the invention is to provide a method for protection of sites of human skin from ultraviolet ray using the cosmetic composition of the invention.

DISCLOSURE OF THE INVENTION

According to this invention the above object and advantages can be attained by an ultraviolet ray-absorbing cosmetic composition for application to skin containing particles having less than 3 μm of average diameter of a cyclic imino ester represented by the following formula (I)

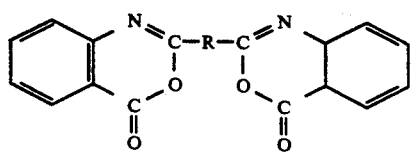

(wherein R is a divalent aromatic hydrocarbon residue) in a quantity effective for absorption of ultraviolet ray, together with at least one cosmetic base selected from the group consisting of hydrocarbons, fatty acid geycerides, waxes, fatty acids and their esters, alcohols, and inorganic pigments.

In the above formula (I) R is a divalent aromatic hydrocarbon residue. Preferred examples of these aromatic hydrocarbon residues include phenylene, biphenylene and naphthylene. Two bonds of these aromatic hydrocarbon groups can be present in optional position. For example, there can be mentioned as more specific examples o-, m- or p-phenylene, 4,4'-biphenylene, 3,3'-biphenylene, 1,5-naphthylene, 2,6-naphthylene, etc.

Further, these aromatic hydrocarbon groups can be substituted. Examples of such substituents include lower alkyl group having 1 to 4 carbon atoms, nitro group, halogen atom, etc. The lower alkyl group having 1 to 4 carbon atoms may be either straight chain or branched chain, and can be any of methyl, ethyl, n-propyl, isopropyl, n-butyl, isobutyl, sec-butyl, and t-butyl. Among them methyl is particularly preferred. Examples of halogen include fluorine, chlorine, bromine, etc. Among them chloro is particularly preferred.

Examples of the cyclic imino esters represented by the above formula (I) include
2,2'-p-phenylenebis(3,1-benzoxazin-4-one),
2,2'-(4,4'-biphenylene)bis(3,1-benzoxazin-4-one),
2,2'-(2,6-naphthylene)bis(3,1-benzoxazin-4-one),
2,2'-(1,5-naphthylene)bis(3,1-benzoxazin-4-one),
2,2'-(2-methy-p-phenylene)bis(3,1-benzoxazin-4-one),
2,2'-(2-nitro-p-phenylene)bis(3,1-benzoxazin-4-one),
2,2'-(2-chloro-p-phenylene)bis(3,1-benzoxazin-4-one), These compounds can be prepared according to processes per se known.

For example, there can be used a process which comprises reacting anthranilic acid with an aromatic dicarboxylic acid dichloride according to the process disclosed in the specification of U.S. Pat. No. 3,408,326 to form an N,N'-bis-2-carboxyphenyl-substituted aromatic dicarboxylic acid diamide, and then heating the above diamide together with acetic anhydride to dehydrate and cyclize it.

The above process can be represented by the following reaction formula with respect to the case of using terephthalic acid dichloride as the aromatic dicarboxylic acid dichloride:

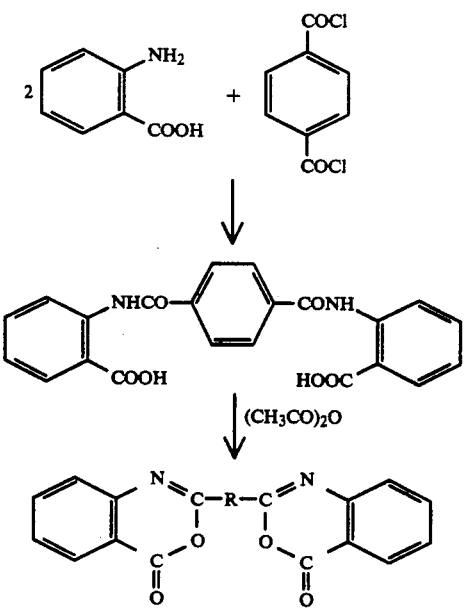

Further as an alternative process it is also possible to adopt a process which comprises reacting isatoic anhydride with an aromatic dicarboxylic acid dichloride in pyridine according to the method disclosed in the gazette of West German Laid-Open Patent Publication No. 2,556,590 and the gazette of the corresponding Japanese Laid-Open Patent Publication No. 100,086/1976.

The above process can be represented by the following reaction formula with respect to the case where biphenylene-4,4'-dicarboxylic acid dichloride is used as the aromatic dicarboxylic acid dichloride:

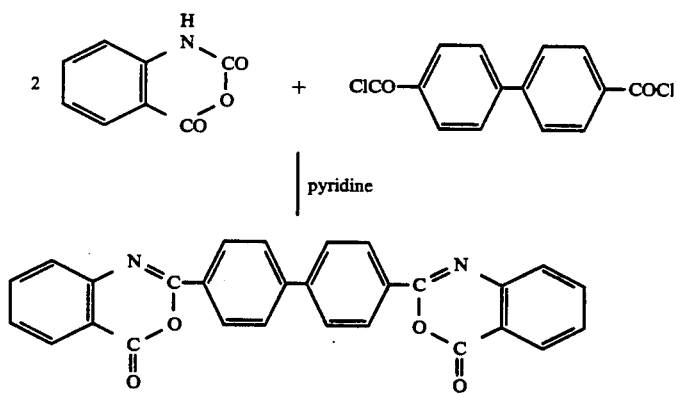

It has been revealed by research of the inventors that since the cyclic imino esters represented by the above formula (I) have an excellent ultraviolet ray-absorbing ability and are excellent in water resisting stability, they sustain the ultraviolet ray-absorbing ability over a long time, and moreover that since these esters are sparingly soluble in organic solvents, fats and oils and sebum, they are compounds which are not percutaneously absorbed and are stable and moreover have a low stimulating property to the skin and can prevent aging of the skin.

The cosmetic composition of the invention, wherein particles having less than 3 μm of average diameter of the cyclic imino ester compounds are compounded into the above cosmetic bases, have no aging effect of the skin caused by exposing the skin to sunlight for a long period and no side effect, and are safe compounds which can absorb ultraviolet ray and can thereby prevent occurrence of erythema on/in the skin.

In the inventive cosmetic composition, the cyclic imino ester (I) is contained as particles with 3 μm or less of the average particle diameter or, preferably, as particles with 1 μm or less of the average particle diameter.

The cosmetic composition containing a cyclic imino ester with 3 μm or less of the average particle diameter may be obtained by applying either of (1) the method in which the cyclic imino ester is turned into particles with 3 μm or less of the average particle diameter in advance by applying a physical pulverizing method such as wet pulverizing, dry pulverizing or the like followed by compounding thereof together with the cosmetic base material, and (2) the method in which the cyclic imino ester with the average particle diameter exceeding 3 μm is brought in a suspension by being added to water, an organic solvent or a solvent mixture thereof followed by pulverizing in the presence or absence of the cosmetic base material by using a wet granulator to be turned into particles with 3μm or less of the average particle diameter with further addition of, if required, the cosmetic base material to be compounded.

The cosmetic base material for the inventive cosmetic composition comprise hydrocarbons including liquid paraffin, paraffin wax, microcrystalline wax, ozocerite, vaseline and squalane; fatty acid glycerides including olive oil, castor oil, rice-bran oil, sesame oil and Japan wax; waxes including lanolin, candelilla wax, montan wax and rice wax; fatty acids including lauric acid and stearic acid; fatty acid alkyl esters including isopropyl palmitaste and isopropyl myristate; glycerine monooleate; aliphatic alcohols including ethyl alcohol, cetyl alcohol, palmityl alcohol and lanolin alcohol, 1,2-propylene glycol, glycerine and sorbitol; and inorganic pigments including titanium oxide, talc and kaolin.

When classified by application site or use, the cosmetic composition of the invention can be, for example cream for face; make-up products such as make-up cake or foundation, make-up lotion, make-up powder, or make-up cream; lotion or astringent for face; body oil or lotion; hand lotion or cream; or the like.

Although the quantity of the ultraviolet ray-absorbing compound to be compounded in the cosmetic composition of the invention varies depending on what extent of protective effect against ultraviolet ray is intended to be attained, it is generally desirable that the quantity is in the range 0.2 to 20 % by weight based on the weight of the whole composition. Not only one of the ultraviolet ray-absorbing compounds but also two or more thereof can be compounded, and further it is also possible to use it together with known ultraviolet ray absorber.

The cosmetic composition of the invention can contain usual auxiliary agents for cosmetics such as foaming agent, pigment, dye, softening agent, metallic soaps, lubricant, surfactant, antioxidants, antiseptic agent, antifoamin agent and perfume, vitamines, hormones, and other optional components directly used in cosmetic compositions.

The present invention is further described in more detail below by examples. Parts in the examples represent weight parts.

EMBODIMENTS

Reference Example (Preparation of Cyclic Imino Ester)

Anthranilic acid (14.0 parts) and 11.7 parts of sodium carbonate were dissolved in 250 parts of water, and a solution obtained by dissolving 10.1 parts of terephthalic acid dichloride in 60 parts of acetone was added dropwise to the above solution with stirring at 20 to 30° C. Reaction was carried out at room temperature for 2 hours after the dropwise addition and further under acetone reflux for one hour. Then, concentrated hydrochloric acid was added to make the reaction system acidic, and the precipitate was filtered and dried to obtain 19.1 parts of terephthaloyl-bisanthranilic acid.

Then, 100 parts of acetic anhydride was added to the whole quantity of the compound, and reaction was carried out under reflux of acetic anhydride for 2 hours. The reaction mixture was cooled, and the precipitate was filtered and dried to obtain 15.5 parts of 2,2'-p-phenylenebis (3,1-benzoxazin-4-one) having average diameter of 25 μm.

Further, the same procedures as above were carried out except that 4,4'-diphenyldicarboxylic acid dichloride and naphthalene-2,6-dicarboxylic acid dichloride were used respectively in place of terephthalic acid dichloride, whereby 2,2'-(4,4'-diphenylene)bis (3,1-benzoxazin-4-one) having average diameter of 31 μm and 2,2'-(2,6-naphthylene)bis-(3,1-benzoxazin-4-one) having average diameter of 19 μm were obtained respectively.

Each of the cyclic imino esters obtained herein was subjected to pulverization using a Jet Dry Granulator manufactured by K. K. Seishin Kigyo to give 2,2'-phenylene bis(3,1-benzoxazine-4-one) with 0.8 μm of the average particle diameter, 2,2'(4,4'-diphenylene) bis(3,1-benzoxazin-4-one) with 1.1 μm of the average particle diameter or 2,2'-(2,6-naphthylene) bis(3,1-benzoxazine-4-one) with 0.9 μm of the average particle diameter for the following tests.

The determination of average particle diameter was carried out using a Laser Scattering Particle Size Distribution Analyzer Model LA-700 manufactured by K. K. Horiba Seisakusho.

EXAMPLE 1

(Measurement of Ultraviolet Ray-Absorbing Ability)

Ultraviolet ray-absorbing ability was measured for the cyclic imino esters of the invention and a commercially available known ultraviolet absorber (4-t-butyl-4'-methoxy-dibenzoylmethane).

The measurement was carried out using 1,1,2,2-tetrachloroethane as a solvent and Hitachi 330 type spectrophotometer under the conditions of an ultraviolet absorber concentration of $5 \times 10^{-4}$ g/100 ml and an optical path length of 1 cm. The results are shown in Table 1.

TABLE 1

|  | λmax (nm) | (E 1%, 1 cm) | λs (nm) |
| --- | --- | --- | --- |
| 2,2'-p-phenylenebis (3,1-benzoxazin-4-one) | 350 | (1270) | 385 |
| 2,2'-(4,4'-diphenylene)bis(3,1-benzoxazin-4-one) | 348 | (1300) | 395 |
| 2,2'-(2,6-naphthylene) bis(3,1-benzoxazi-4-one) | 354 | (1070) | 400 |
| (Comparative example) 4-t-butyl-4'-methoxy- | 360 | (1040) | 400 |

TABLE 1-continued

| | λmax (nm), (E 1%, 1 cm) | λs (nm) |
|---|---|---|
| dibenzoylmethane | | |

Note:
λmax and λs represent maximum absorption wavelength and absorption initiation wavelength (Measurement of Solubility)

The cyclic imino esters of the invention and the comparative sample were measured for solubility in water, alcohols and oily cosmetic bases at 15° C.

The results are shown in Table 2.

TABLE 2

| | Solubility (mg/l) | |
|---|---|---|
| | (Present invention) 2,2'-p-phenylenebis (3,1-benzoxazin-4-one) | (Comparative example) 4-t-butyl-4'-methoxy-y dibenzoylmethane |
| Water | 0.2 | 0.2 |
| 96 vol % Ethanol | 0.3 | $1.6 \times 10^4$ |
| Glycerin | 0.4 | $2.5 \times 10^3$ |
| Light liquid paraffin | 2 | $8.5 \times 10^3$ |
| Isopropyl myristate | 15 | $5.3 \times 10^4$ |
| Olive oil | 20 | $1.9 \times 10^4$ |
| Castor oil | 19 | $9.6 \times 10^4$ |

It is apparent from the above Table 2 that the cyclic iminoester of the invention has a smaller solubility in the organic solvents and thus smaller absorbability into human body compared to the comparative sample, and that from the above reason the cyclic iminoester of the invention has a higher safety on human bodies.

EXAMPLE 3

(Measurement of Water Resisting Stability)

Fifty milliliters each of aqueous suspensions containing 10% by weight of the cyclic imino esters of the present invention and the comparative samples, respectively was prepared, and allowed to stand in a constant temperature bath of 80° C. for 2 hours.

Then, 50 ml of isopropyl alcohol was added thereto, and the water and the solvent were removed using a rotary evaporator, and the residue was taken out.

This residue was measured for molecular extinction coefficient in max according to a similar manner to Example 1, and its change was used as a measure of water resisting stability.

Water resisting stability (%) =

$$\frac{\text{Molecular extinction coefficient of sample after water resistance test}}{\text{Molecular extinction coefficient of sample before water resistance test}} \times 100$$

Further, the samples before and after hot water treatment were measured for TG-DTA, and its change was examined.

The results are shown in Table 3.

TABLE 3

| | Water resisting stability (%) | Change of TG-DTA |
|---|---|---|
| Present invention | | |
| 2,2'-p-phenylenebis(3,1-benzoxazin-4-one) | 96.9 | no change |
| 2,2'-(4,4'-diphenylene)bis(3,1-benzoxazin-4-one) | 97.6 | same as above |
| 2,2'-(2,6-naphthylene)bis(3,1-benzoxazin-4-one) | 96.7 | same as above |
| Comparative sample | | |
| 4-t-butyl-4'-methoxy-dibenzoyl-methane | 89.4 | generation of subpeak |
| 4-methoxy-2'-sodium carboxylate-dibenzoylmethane | 52.0 | same as above |

It is seen from the above Table 3 that the cyclic imino esters of the invention are superior to the comparative samples in stability against water and have a sustained ultraviolet ray-absorbing effect.

EXAMPLE 4

(Primary Irritation to the Skin)

This experiment was carried out according to the following method.

1) Eight white rabbits (weighing 2.0 to 3.0 kg) whose fur on the back was cut are grouped into two groups each consisting of 4 animals. Animals of one group (blank) were fixed as they were in braces respectively, and those of the other group were fixed in braces respectively after excoriation was formed at the site to be tested.

2) Vaseline base containing 25% by weight of a test substance was applied onto a lint cloth, and the resulting lint cloth was stuck on the surface of the skin.

3The whole body of the rabbit was wrapped with moisture-proof rubber for dental use to prevent movement of the stuck lint cloth and at the same time evaporation of volatile substance.

4) Twenty-four hours thereafter the lint cloth was removed and the site to be tested was observed. Second and third observations are made 48 and 72 hours thereafter, respectively. The average of evaluation after 24 and 72 hours was calculated as a final evaluation point.

5) Evaluation was made by independently judging formation of erythema and eschar, and edema, specifically according to the following criteria. Formation of erythema and eschar:

| | |
|---|---|
| No erythema | — |
| Very slight erythema (barely perceptible) | ± |
| Well defined erythema | + |
| Moderate to severe erythema | ++ |
| Severe erythema (beet redness) erythema to slight formation of eschar | +++ |
| Formation of edema | |
| No edema | — |
| Very slight edema (barely perceptible) | ± |
| Slight edema (edge of area well defined by definite raising) | + |
| Moderate edema (raised approximately 1 mm) | ++ |
| Severe edema (raised more than 1 mm and extending beyond area of exposure) | +++ |

The results are shown in Table 4.

TABLE 4

| Formation of erythema or eschar | Cyclic imino ester | | |
|---|---|---|---|
| | A | B | C |
| − | 4/4 | Same as left | Same as left |
| ± | 0/4 | Same as left | Same as left |
| + | 0/4 | Same as left | Same as left |
| + + | 0/4 | Same as left | Same as left |
| + + + | 0/4 | Same as left | Same as left |
| Formation of edema | 0/4 | 0/4 | 0/4 |

A, B and C in Table 4 are as follows:
A: 2,2'-p-phenylenebis(3,1-benzoxazin-4-one)
B: 2,2'-(4,4'-diphenylene)bis(3,1-benzoxazin-4-one)
C: 2,2'-(2,6-naphthylene)bis(3,1-benzoxazin-4-one)

Formation of erythema or eschar and formation of edema were not observed for the three cyclic imino esters.

EXAMPLE 5

(Mutagenicity)

This experiment was carried out based on "About Test on Mutagenicity Using Microorganisms", a notification of the Director of the Standard Bureau, the Ministry of Labor, Japan dated May 18, 1985.

No mutagenicity was observed for any of the same cyclic imino esters A, B and C as used in Example 4.

EXAMPLE 6

(Allergic Contact Dermatitis Test)

Method: This experiment was carried out as follows based on (Guinea Pig Maximization Test (Magnusson, B. & Klingman, A. M: Usefulness of guinea pig tests for detection of contact sensitizers, In Advances in Modern Toxicology. Vol 4, pp 551–560 Hemisphere Publishing Co., Washington & London, 1977)

1) The fur on the scapula of white female guinea pigs weighing 300 to 500 g was cut in an area of 4×6 cm.
2) Each sample was intrademally injected into the positions of (1), (2) and (3) in FIG. 1.
   (1) 0.1 ml of Freund's complete adjuvant alone
   (2) 0.1 ml of test substance alone
   (3) sample w/o emulsified with 0.1 ml of Freund's complete adjuvant
3) The fur at the sites was cut one week after the intradermal injection, and the test substance was a nonirritating test substance, 10% sodium lauryl sulfate (vaseline base) was applied thereon.
4) Vaseline containing 25 % by weight of the test substance was spread on a filter paper of 2×4 cm and occlusive pasting was conducted for 48 hours.
5) The fur at the side of the body (4) was cut in an area of 5×5 cm two weeks after the occlusive pasting.
6) The test substance was applied onto a filter paper of 2×2 cm, and occlusive pasting was conducted for 24 hours.
7) Measurement was carried out according to the following criterion:

| Symbol | Criterion of Judgement |
|---|---|
| 0 | No reaction |
| 1 | Light or polynesic erythema |
| 2 | Diffuse erythema in middle degree |
| 3 | Strong erythema plus edema |

Results are shown in Table 5 in case where the cyclic imino esters A, B and C used in Example 4 were used as test substance.

TABLE 5

| Judgement | Cyclic imino ester | | |
|---|---|---|---|
| | A | B | C |
| 0 | 4/4 | Same as left | Same as left |
| 1 | 0/4 | Same as left | Same as left |
| 2 | 0/4 | Same as left | Same as left |
| 3 | 0/4 | Same as left | Same as left |

Contact sensitization was not observed for any of these compounds.

EXAMPLE 7

(Contact Photosensitization)

This experiment was conducted as follows based on Adjuvant-Strip method (Seinichi Hifu, 432 (5), 831–837, 1980).

(1) Hartley white guinea pigs weighing 370 to 420 g were used.
(2) The fur at the cervical part of the guinea pigs was cut by an electric hair clipper, and the part was further shaved with an electric razor.
(3) A section of 2×4 cm was set at the cervical part, and 0.1 ml portions of Freund's complete adjuvant w/o emulsified with sterilized distilled water were intradermally injected at the four corners.
(4) The skin of the section of 2×4 cm was subjected to stripping with cellophane tape to cause light erythema.
(5) 0.1 ml of vaseline containing 25% by weight of the test substance was applied onto this site.
(6) After the application, 6 lamps in total, namely 3 sunlamps (Toshiba FL-40SE30) and 3 black lights (Toshiba FL-40SBLB) were arranged in parallel, 70 minutes irradiation was carried out at a distance of 10 cm from the light sources. Total energy of the irradiation at this time was 12.0 J/cm$^2$.
(7) The procedures (4), (5) and (6) were repeated 5 times every other day.
(8) Two weeks after completion of the sensitization, the fur on the whole back of the guinea pig was cut, and the resulting whole back was epilated for 15 minutes with an emulsion type epilating cream containing 3.3% of thioglycolic acid.
(9) 24 Hours after the epilation, 4 sections each of 1.5 cm×1.5 cm were set in two rows using the medium line as a symmetry axis.
(10) This site was coated with the test substance and irradiated for 70 minutes at a distance of 10 cm from 6 black lights. Total energy at this time was 10.2 J/cm$^2$.
(11) Judgement was made 24 and 48 hours after the irradiation according to the following criterion:

| [Judgement criterion] Formation of erythema | |
|---|---|
| No erythema | 0 |
| Erythema in very light degree | 1 |
| Distinct erythema | 2 |
| Erythema in middle to heavy degree | 3 |
| Heavy erythema wherein reaction is deep and to which slight eschar is added | 4 |

Results are shown in Table 6 in case where the cyclic imino ester A, B and C used in Example 4 were used as test substance.

TABLE 6

| Judgement Formation of erythema | Cyclic imino esters | | |
|---|---|---|---|
| | A | B | C |
| 0 | 10/10 | Same as left | 9/10 |
| 1 | 0/10 | Same as left | 1/10 |
| 2 | 0/10 | Same as left | Same as left |
| 3 | 0/10 | Same as left | Same as left |

Contact photosensitization was not observed at all for the cyclic imino esters A and B. Contact photosensitization was very slightly observed for C, only in a degree which is utterly out of question in practical use.

EXAMPLES 8 AND 9 AND COMPARATIVE EXAMPLES 1-3

(W/O Type Cream)

Cosmetics composition indicated in Table 7 were prepared.

TABLE 7

| | | Example 8 | Example 9 | Comparative Example 1 | Comparative Example 2 | Comparative Example 3 |
|---|---|---|---|---|---|---|
| A) | 2,2'-p-phenylene bis(3,1-benzoxazin-4-one) having average diameter of 0.8 μm | 6 parts | — part | — part | — part | — part |
| | 2,2'-p-phenylene bis(3,1-benzoxazin-4-one) having average diameter of 25 μm | — | 6 | — | 6 | — |
| | 2,2'-(4,4'-diphenylene) bis(3,1-benzoxazin-4-one) having average diameter of 1.1 μm | | | | | |
| | 2,2'-(4,4'-diphenylene)bis (3,1-benzoxazin-4-one) having average diameter of 31 μm | — | — | — | — | 6 |
| | Myristic acid isopropyl ester | 10 | 10 | 10 | 10 | 10 |
| | Vaseline | 10 | 10 | 16 | 10 | 10 |
| | Salt of sulfuric ester of alcohol by reductin of tallow (sulfation rate 10%) | 15 | 15 | 15 | 15 | 15 |
| | 4-Hydroxybenzoic acid propyl ester | 0.1 | 0.1 | 0.1 | 0.1 | 0.1 |
| B) | Glycerin | 1.5 | 1.5 | 1.5 | 1.5 | 1.5 |
| | 1,2-Propylene glycol | 1.5 | 1.5 | 1.5 | 1.5 | 1.5 |
| | Aqueous sorbitol solution | 4 | 4 | 4 | 4 | 4 |
| | Water | about 100 | about 100 | about 100 | about 100 | about 100 |

Composition A) was mixed with heating to about 70° C., and added to the water layer composition B) warmed to about 70° C. After stirring, the mixture was cooled to about 40° C., perfume was added thereto and the mixture was homogenized.

Skin protection test against UV-A

This test was carried out using guinea pigs (one group of 7 animals) based on the method of Nakayama, et al. (Sunlight and Man page 59, published by Todai Shuppan, 1974).

Previously, 8 mg/kg of 8-methoxysoralen was orally administered to the guinea pigs to enhance sensitivity to UV-A.

Creams of Exmaples 8 and 9 and Comparative Exmaples 1-3 were applied onto the skin which was shaved on the back, and effects in the examples were compared to those in case of non-application and in case of Comparative example using as a light source Toshiba FL-40BLB lamp (max 360 nm).

The results are shown in Table 8. Each value means number of animals in which erythema was formed at each irradiation time.

TABLE 8

| Irradiation time (min.) | Example 8 | Example 9 | Comparative Example 1 | Comparative Example 2 | Comparative Example 3 | Non-application |
|---|---|---|---|---|---|---|
| 4 | 0 | 0 | 0 | 0 | 0 | 2 |
| 6 | 0 | 0 | 1 | 0 | 0 | 7 |
| 8 | 0 | 0 | 3 | 0 | 1 | 7 |
| 10 | 0 | 0 | 5 | 1 | 1 | 7 |
| 15 | 0 | 0 | 7 | 1 | 2 | 7 |
| 20 | 0 | 0 | 7 | 3 | 3 | 7 |
| 30 | 0 | 0 | 7 | 3 | 3 | 7 |

Table 8 indicates that Examples 8 and 9 perfectly protect the skin from UV-A compared to the case of non-application and Comparative examples and thus have an excellent effect as a cosmetic composition for prevention of sunburn.

EXAMPLE 10

(O/W Type Cream)

| | | |
|---|---|---|
| A) | 2,2'-p-phenylenebis(3,1-benzoxazin-4-one) | 8 parts |
| | Saturated fatty acid triglyceride having 8 to 10 carbon atoms | 10 |
| | Cetyl alcohol | 1.5 |
| | Emulsified mixture of stearyl alcohols, cetyl alcohol and their ethylene oxide adducts | 8 |
| | 4-Hydroxybenzoic acid propyl ester | 0.1 |
| B) | Glycerin | 1.5 |
| | 1,2-Propylene glycol | 1.5 |
| | Aqueous sorbitol solution | 4 |
| | Water | about 100 |

Composition A) was mixed with warming to about 70° C., the mixture was added to the water layer composition B) warmed to about 70° C. followed by mixing with stirring, and the resulting mixture was cooled to about 40° C. and homogenized after addition of perfume.

EXAMPLE 11

(Emulsion)

| | |
|---|---|
| 2,2'-(2,6-naphthylene)bis(3,1-benzoxazin-4-one) | 10 parts |
| Gosspol wax | 5 |
| Vaseline oil | 6 |
| Myristic acid isopropyl ester | 3 |
| 4-Hydroxybenzoic acid propyl ester | 0.3 |
| Glycerin | 20 |
| Water | about 56 |

The above composition was mixed with stirring, and after addition of perfume the mixture was homogenized.

EXAPLE 12

(Oil Foundation)

| | |
|---|---|
| Liquid paraffin | 15 parts |
| 2,2'-p-phenylenebis(3,1-benzoxazin-4-one) | 15 |
| Palmitic acid isopropyl ester | 10 |
| Lanolin alcohol | 3 |
| Microcrystalline wax | 7 |
| Candelilla wax | 0.5 |
| Ozocerite | 8 |
| Titanium oxide | 8 |
| Kaolin | 18 |
| Talc | 6 |
| Red iron oxide | 1.5 |
| Black iron oxide | 0.5 |
| 4-Hydroxybenzoic acid propyl ester | 0.3 |

The above composition was mixed with stirring, and after addition of perfume the mixture was homogenized.

Figure 1:
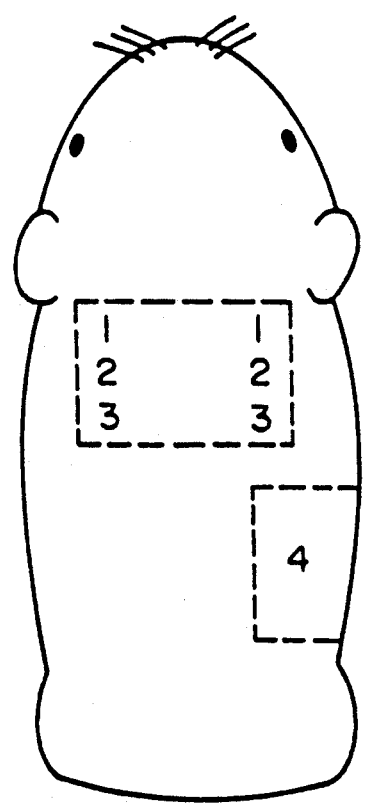
FIG. 1, is a typical drawing of a guinea pig which, in a test to investigate contact sensitization of the ultraviolet ray-absorbing compound to be used in the invention, indicates the place where the compound is adhered.

What is claimed is:

1. An ultraviolet ray-absorbing cosmetic composition for application to skin, consisting essentially of an aqueous suspension of a cyclic imino ester represented by the following formula (I)

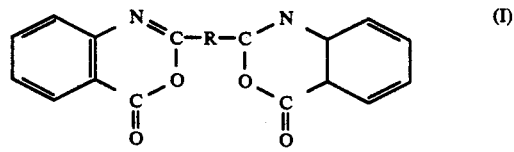

wherein R is a divalent aromatic hydrocarbon residue, said cyclic imino ester having a particle size of less than 3 μm in average diameter in said aqueous suspension, and being present in said aqueous suspension in a quantity effective for absorption of ultraviolet ray, together with at least one cosmetic base selected from the group consisting of hydrocarbons fatty acid glycerides, waxes, fatty acids, alkyl esters of fatty acids, aliphatic alcohols, polyhydric alcohols and inorganic pigments.

2. The cosmetic composition of claim 1 wherein the cyclic imino ester of the formula (I) is used wherein R is phenylene, diphenylene or naphthylene.

3. The cosmetic composition of claim 1 which is cream, foundation, powder, stick or oil.

4. A method for protecting a site of human skin against ultraviolet ray, which comprises applying a cosmetic composition of claim 1 to said site.

* * * * *